(12) United States Patent
Brechbühl et al.

(10) Patent No.: US 12,070,372 B2
(45) Date of Patent: Aug. 27, 2024

(54) DENTAL TORQUE WRENCH

(71) Applicant: STRAUMANN HOLDING AG, Basel (CH)

(72) Inventors: Tobias Brechbühl, Basel (CH); Alain Hedinger, Basel (CH)

(73) Assignee: STRAUMANN HOLDING AG, Basel (CH)

(*) Notice: Subject to any disclaimer, the term of this patent is extended or adjusted under 35 U.S.C. 154(b) by 524 days.

(21) Appl. No.: 17/416,886

(22) PCT Filed: Dec. 17, 2019

(86) PCT No.: PCT/EP2019/085735
§ 371 (c)(1),
(2) Date: Jun. 21, 2021

(87) PCT Pub. No.: WO2020/127331
PCT Pub. Date: Jun. 25, 2020

(65) Prior Publication Data
US 2022/0031432 A1 Feb. 3, 2022

(30) Foreign Application Priority Data
Dec. 19, 2018 (EP) .................................... 18214056

(51) Int. Cl.
*A61C 8/00* (2006.01)
*B25B 13/46* (2006.01)
*B25B 23/142* (2006.01)

(52) U.S. Cl.
CPC .......... *A61C 8/0089* (2013.01); *B25B 13/463* (2013.01); *B25B 23/1427* (2013.01)

(58) Field of Classification Search
CPC . A61C 1/186; A61C 8/0089; A61B 2090/031; A61B 17/8875; A61B 17/8883;
(Continued)

(56) References Cited

U.S. PATENT DOCUMENTS 1,464,128 A * 8/1923 Coes ...................... B25B 13/46
 81/472
6,988,430 B1 * 1/2006 Putney .................. B25B 13/462
 81/60
(Continued)

FOREIGN PATENT DOCUMENTS

CN 107303202 A * 10/2017 ........... A61C 8/0089
DE 202004014195 U1 11/2004
(Continued)

OTHER PUBLICATIONS

Jan. 29, 2020 International Search Report issued in International Patent Application No. PCT/EP2019/085735.
(Continued)

*Primary Examiner* — Jacqueline T Johanas
*Assistant Examiner* — Shannel Nicole Belk
(74) *Attorney, Agent, or Firm* — Oliff PLC (57) ABSTRACT

A torque wrench as a ratchet instrument for medical technology, including receiving opening which has head region, neck region adjoining head region, rod-shaped actuating lever fastened to neck region for application of torque to the head region, and enclosure forming receiving opening of head region. Furthermore, torque wrench includes spring clip and latching lug formed thereon. The latching lug in rest position of latching lug protrudes into receiving opening and in entraining portion of latching lug is intended to interact with counterpart surface of insertion instrument inserted into enclosure during rotation in tightening direction of actuating lever in entraining position. The latching lug is intended to move into release position during rotation contrary to tightening direction against force of spring clip, in order to provide free running between head region and insertion instrument. The enclosure has break extending over entire cross-section of enclosure and forms spring clip.

20 Claims, 4 Drawing Sheets

(58) Field of Classification Search
CPC ............ A61B 17/8886; A61B 17/8891; B25B 13/463; B25B 13/462; B25B 23/1427; B25B 23/1422; B25B 23/142; B25B 23/14; B25B 13/52
See application file for complete search history.

(56) References Cited

U.S. PATENT DOCUMENTS

2010/0304330 A1   12/2010  Rasmussen
2015/0027277 A1    1/2015  Waizenegger

FOREIGN PATENT DOCUMENTS

| DE | 102012101050 B3 | 1/2013 | |
|----|----|----|----|
| DE | 102017000222 A1 | 7/2018 | |
| EP | 0704281 A1 | 4/1996 | |
| WO | 2009/036943 A1 | 3/2009 | |
| WO | WO-2009036943 A1 * | 3/2009 | ............ A61B 17/862 |

OTHER PUBLICATIONS

Jan. 29, 2020 Written Opinion issued in International Patent Application No. PCT/EP2019/085735.

* cited by examiner

DENTAL TORQUE WRENCH

The invention relates to a torque wrench as a ratchet instrument for medical technology, in particular dentistry, according to the preamble of claim 1.

In dentistry it is known for implants to be inserted into the maxillary bone, and for connecting elements such as abutments to be fastened to the implants, on which the superstructure, in particular a crown or a bridge, is then placed. In order for the implant or the connecting element, respectively, to be screwed in, a driver instrument can be placed in a form-fitting manner on the free end of said implant or connecting element, respectively, and the driver instrument rotated by a torque wrench. The long-term stability and reliability of the screw fitting depend on the latter being performed with the respective optimum torque. Insufficient tightening can later lead to the screw fitting being loosened, while excessive tightening causes an overload on the inserted connecting element and the implant, increasing the risk of the latter breaking, or causing damage to the bone, respectively.

A torque wrench having a ratchet function for application in dentistry is disclosed in EP 0 704 281 A1. The torque wrench comprises a torque instrument, in particular a ratchet instrument, as well as a torque indicator which as an accessory can be attached to said ratchet instrument. The torque indicator possesses a sleeve-shaped support which can be pushed onto a handle of the torque instrument and to which an elastic flexural bar is fastened. When activated, a force in the tightening direction of the torque wrench is exerted on the free end of the flexural bar, and the torque generated is indicated on a scale. The cleaning and sterilization of this torque wrench requires the torque wrench to be disassembled and is thus relatively complex. Furthermore, the production of said torque wrench is relatively expensive by virtue of the multiplicity of components.

A torque wrench as a ratchet instrument for medical technology is known from DE 20 2004 014 195 U1, said torque wrench comprising a frontmost head region, an adjoining neck region which is followed by a shaft region, and a handle region which is disposed so as to be very rear. The head region, the neck region, the shaft region and the handle region extend in one plane. The torque wrench furthermore comprises a receptacle opening which is provided in the head region, is surrounded by a bezel, and possesses a center through which an axis extends so as to be perpendicular to the plane. The receptacle opening serves for inserting a driver instrument in the extent of the axis. The torque wrench furthermore comprises a ratchet segment of limited mobility which is disposed on the periphery of the receptacle opening, the front part of said ratchet segment pointing toward the receptacle opening. The front part is specified, when the torque wrench is activated in the screw-in mode, for engaging in an entraining manner with an external contour present on the head of the driver instrument, and when the torque wrench is activated in the reverse direction, thus in the ratchet mode, for releasing the entraining engagement with the external contour present on the head of the driver instrument. The torque wrench furthermore comprises a flexurally stiff base shank which from the neck region extends along the shaft region. A ratchet spring extends from the ratchet segment into the neck region, wherein the ratchet segment and the ratchet spring form an integral ratchet. Long thin slots which permit the ratchet to deflect, counter to the force of the ratchet spring, in the plane are configured on both sides of the ratchet. The ratchet is furthermore formed integrally from the neck region. As a result of the integral embodiment of this torque wrench, the disassembling for the cleaning and sterilization is dispensed with. However, the long thing slots on both sides of the ratchet complicate the cleaning of the torque wrench.

It is thus an object of the present invention to provide a torque wrench for medical technology, in particular for dentistry, which can be produced in a cost-effective manner and easily cleaned.

This object is achieved according to the invention by a torque wrench according to claim 1. Preferred embodiments of the invention are set forth in the dependent claims.

The invention relates to a torque wrench as a ratchet instrument for medical technology, in particular dentistry. The torque wrench comprises a head region which has a receptacle opening, a neck region which adjoins the head region, a bar-shaped activation lever which, for applying a torque to the head region, is fastened to the neck region and extends at least approximately in one plane, preferably in the plane, and a bezel which forms the receptacle opening of the head region. The neck region forms an at least approximately cuboid, preferably solid, part. The bezel defines a rotation axis that runs so as to be at least approximately orthogonal, preferably orthogonal, to the plane, and is specified for receiving a driver instrument in the extent of the rotation axis. The plane may comprise a front side of the torque wrench, and a further plane which runs parallel to the plane may comprise a rear side of the torque wrench.

The torque wrench furthermore comprises a spring bracket and a latching cam which is configured on said spring bracket and in the resting position of said latching cam protrudes into the receptacle opening. The resting position is the position of the latching cam when no driver instrument is inserted in the receptacle opening and no force in the radial direction is exerted on the spring bracket.

The latching cam has an entrainment portion which, when the driver instrument is inserted in the receptacle opening, and when the activation lever is rotated in the tightening direction in an entraining position of the latching cam, is specified for interacting with a mating face of the driver instrument. The entraining position may correspond to the resting position when the spring bracket exerts at least approximately no force on the inserted driver instrument. When the entrainment portion interacts with the mating face, a torque is transmitted to the driver instrument by way of a form-fitting entrainment.

The latching cam, when rotating counter to the tightening direction, is specified for moving counter to the force of the spring bracket in a radially outward direction to a releasing position, so as to form a freewheeling mechanism between the head portion and the driver instrument.

The bezel according to the invention has a cutout running across the entire cross section of the latter and forms the spring bracket.

In one preferred embodiment, the latching cam is configured so as to be integral to and in one piece with the spring bracket. This simplifies the cleaning because any deposition of dirt at a connecting location between the latching cam and the spring bracket is prevented.

In one preferred embodiment, the entrainment portion is formed by an entrainment face which runs so as to be at least approximately radial to the rotation axis and is specified for interacting with the mating face of the inserted driver instrument that preferably runs so as to be at least approximately radial to the rotation axis. This configuration of the entrainment face and of the mating face enables a reliable entrainment of the driver instrument.

Furthermore, the length of the entrainment face measured radial to the rotation axis, said entrainment face coming into contact with the mating face of the driver instrument, here referred to as the operating length, can likewise be used as a parameter for guaranteeing a reliable entrainment of the driver instrument. The operating length corresponds to the length of the required movement of the latching cam, in a radially outward manner in terms of the rotation axis, such that the latching cam can reach the releasing position thereof. A short operating length can consequently be advantageous, because the resulting deformation of the spring bracket is correspondingly small, the deformation thus remaining within the elastic range of the spring bracket. When the torque wrench is used, an excessively short operating length can however result in the entrainment portion in terms of the rotation axis slipping radially outward by the operating length because of an undesirable movement of the torque wrench in terms of the driver instrument on the mating face, and the latching cam consequently disengaging from the entraining position. The radial length of the entrainment face is preferably larger than or equal to the radial length of the mating face in order for the transmission of force to be optimized. The radial length of the entrainment face is preferably between 0.2 mm and 5 mm in order for the transmission of force to be optimized.

In one preferred embodiment, the latching cam is adjacent to the cutout. The latching cam is particularly preferably directly adjacent to the cutout. The wrapping angle of the present spring bracket about the inserted driver instrument is thus maximized. As a result of the wrapping, additional static friction forces in the circumferential direction are created between the spring bracket and the inserted driver instrument, said additional static friction forces facilitating the retention of the driver instrument in the receptacle opening. This has the effect that the force acting in the circumferential direction on the entrainment portion of the latching cam is smaller during rotation in the tightening direction.

In one preferred embodiment, the latching cam has an engagement face which, when viewed in the tightening direction, trails the entrainment face and preferably adjoins the entrainment face, said engagement face permitting the movement of the latching cam to the releasing position and consequently the freewheeling mechanism. When the activation lever is rotated counter to the tightening direction, the engagement face forms the face by way of which the force of the spring bracket is exerted on the driver instrument.

The engagement face is particularly preferably formed by a taper, the spacing of the latter from the rotation axis increasing counter to the tightening direction and permitting the freewheeling mechanism. The spacing preferably increases without any interruption, so as to enable a continuous freewheeling mechanism which has a consistent friction between the engagement face and the driver instrument. The torque wrench thus performs the ratchet function thereof in a jolt-free manner.

In one particularly preferred embodiment, the taper extends at least approximately up to the free end of the spring bracket. This enables a simple production of the circumferential face of the spring bracket that faces the rotation axis.

The engagement face particularly preferably has an extension face which, when viewed in the tightening direction, trails the entrainment face, runs in the circumferential direction and is directly adjacent to the entrainment face, the taper adjoining said extension face. The extension face and the taper delimit a volume of the latching cam, said volume serving for preventing the entrainment portion being sheared off during the application of the latter. The wear on the driver instrument by the latching cam when freewheeling can optionally be reduced by said volume, because the latching cam does not have any sharp edge between the entrainment face and the taper.

In one particularly preferred embodiment, the taper has a length which, when measured in the radial direction, is equal to or larger than the operating length. It is avoided on account thereof that the movement of the latching cam to the releasing position, when rotating counter to the tightening direction, is blocked by the driver instrument.

In one particularly preferred embodiment, an angle, measured in the plane E, between the taper and a tangent to the circumferential direction, wherein the tangent runs on the intersection point between the taper and the circumferential direction, is smaller than 45°, preferably between 15° and 45°, particularly preferably between 25° and 40°. The angle is smaller than 45° so that the movement of the latching cam to the releasing position, when rotating counter to the tightening direction, requires little space in the radial direction. The movement of the latching cam can be specifically restricted in particular in the region of the mouth. At an angle between 15° and 45°, the friction force between the surface of the taper and the driver instrument is in a range in which the torque transmitted to the driver instrument by friction, when rotating counter to the tightening direction, for example the freewheeling torque, remains below a releasing torque of the implant or of the connecting element. This is particularly important when implanting in a bone which may be unstable and fragile, in which instance the releasing torque should be small. The freewheeling torque is preferably less than 3 Ncm. Based on experience, an angle between 25° and 40° is optimal in order for the freewheeling torque and simultaneously the radial movement of the latching cam to the releasing position to be optimized.

In one preferred embodiment, the latching cam, when measured in the axial direction, extends across the entire thickness of the bezel. The extent in the axial direction of the latching cam enables a reliable entrainment because this results in a correspondingly larger entrainment face. However, it is also possible for the latching cam to extend across only part of the entire thickness, preferably so as to be centered in terms of the thickness of the bezel when viewed in the axial direction. As a result of the centric position of the latching cam, there are no lateral bending torques which act on the spring bracket.

A conventional driver instrument comprises a cylindrical ratchet head which defines a rotation axis of the driver instrument and can be inserted into the receptacle opening of the torque wrench, and a shaft which adjoins the ratchet head and extends in the direction of the rotation axis. The free end of the shaft has a preferably standardized profile, for example a Torx® profile or a hexagonal head, for interacting with the implant or the connecting element, respectively, such that the driver instrument can transfer the torque applied to the ratchet head to the implant or the connecting element, respectively. The ratchet head has a circumferential face which comprises a contour feature that forms the mating face, so as to enable the torque applied to the torque wrench to be transmitted to the driver instrument. The contour feature may be formed by a groove which runs so as to be preferably parallel to the rotation axis of the driver instrument.

The groove preferably has an at least approximately rectangular cross section, the wall of the latter, which in terms of the entrainment face is the leading wall in the tightening direction, preferably running so as to be at least approximately radial in the direction toward the rotation axis and forming the mating face.

The contour feature preferably comprises a plurality of grooves which are of identical configuration and, when viewed in the circumferential direction, are disposed at identical mutual spacings.

In one preferred embodiment of the torque wrench, the latching cam is configured such that, when measured in the circumferential direction of the bezel, the overall length of the taper, optionally including the extension face, is longer than the width of the groove. It can thus be at least approximately completely avoided that the entire latching cam is pushed into the groove, thus potentially blocking the movement of the latching cam to the releasing position when rotating counter to the tightening direction.

In one preferred embodiment, the spring bracket on the side thereof that faces the rotation axis has a clearance which, when viewed in the tightening direction, is a trailing clearance in terms of the entrainment face. The clearance is preferably at least approximately semicircular. Said clearance is furthermore configured such that a part of the ratchet head that leads the mating face can protrude into the clearance when rotating in the tightening direction. A reliable entrainment of the driver instrument is thus ensured.

In one preferred embodiment, the cutout is adjacent to the neck region. The cutout is preferably formed by a slot which extends so as to be at least approximately radial to the rotation axis. The length of the spring bracket, when measured in the circumferential direction, is thus maximized. Consequently, the wrapping angle of the spring bracket about the inserted driver instrument is maximized in the tightening direction. The cutout is configured in such a manner that the latching cam in terms of the rotation axis can move radially outward at least by the operating length such that said latching cam can reach the releasing position thereof.

In one preferred embodiment, the cutout is configured by a cutting which runs so as to be at least approximately radial. The cutout can thus be easily configured, in particular in the case of a bezel having a thin wall.

In one preferred embodiment, the cutout is configured by a cutting which runs so as to be at least approximately axial. In the case of a bezel having a thicker wall than in the preceding embodiment, the cutout can likewise be easily configured.

In one preferred embodiment, the cutout can be configured in such a manner that the movement of the spring bracket is delimited in the circumferential direction.

The spring bracket on the free end thereof has an end face which is defined by the cutout and runs so as to be at least approximately radial to the rotation axis, and which faces a counter-end face of the neck region that is defined by the cutout and runs so as to be at least approximately radial to the rotation axis.

In one preferred embodiment, the width of the cutout, when measured in the circumferential direction, is sized such that the end face of the spring bracket, when deformed by compression, can at least partially come to bear on the counter-end face of the neck region once the deformation of the spring bracket has reached a predetermined measure. The width of the cutout is determined in such a manner that the deformation of the spring bracket remains in the elastic range of the latter. Any further deformation of the spring bracket, and consequently damage to the torque wrench, can thus be prevented.

The cutout particularly preferably forms a first hook, which projects from the neck region, and a second hook, which projects from the spring bracket. The first hook and the second hook have a first protrusion and a second protrusion, respectively, which run transverse and preferably so as to be orthogonal to the tightening direction and mutually overlap. In the resting state and in the normal operation of the torque wrench, the first protrusion and the second protrusion are mutually spaced apart. This means that the first protrusion and the second protrusion are configured such that a gap is present therebetween in the resting state and in normal operation.

In order to avoid any excessive expansion of the spring bracket, the first protrusion and the second protrusion come to bear on one another once the deformation of the spring bracket as a result of expansion has reached a predetermined measure. Any further deformation of the spring bracket, and consequently damage to the torque wrench, can thus be prevented. Excessive expansion can take place for example when gripping and retrieving the torque wrench from a surgical cassette, for example when the torque wrench and other tools engage in one another and excessive pulling force is exerted on the torque wrench.

The gap is determined in such a manner that the deformation of the spring bracket remains in the elastic range of the latter. This means that the deformation remains reversible and the spring bracket returns to the original shape thereof once a deformation force is no longer applied. It can thus be ensured that the spring bracket retains the characteristics thereof, in particular the exerted force counter to which the latching cam can make its way to the releasing position.

When the external diameter of the ratchet head of the inserted driver instrument is smaller than the internal diameter of the receptacle opening, the gap can be smaller during normal operation than in the resting state.

The cutout which is configured by the cutting that runs so as to be at least approximately radial, when viewed in the longitudinal section of the bezel, can run so as to be at least approximately S-shaped and from the front side to the rear side of the torque wrench, wherein a first half of the S-shape that faces the front side forms the first hook, and a second half of the S-shape that faces the rear side forms the second hook.

It is likewise possible that the cutout which is configured by the cutting that runs so as to be at least approximately axial, when viewed in the cross section of the bezel, runs so as to be at least approximately S-shaped and from an internal side of the bezel that faces the rotation axis to an external side of the bezel that faces away from the rotation axis. In this embodiment, the first half of the S-shape that faces the internal side forms the first hook, and a first half of the S-shape that faces the external side forms the second hook.

In one preferred embodiment, the cutout opens out into a recess which is configured in the neck region and has the first hook. Furthermore, the second hook, which projects from the spring bracket, protrudes into the recess so as to engage with the first hook once the deformation of the spring bracket as a result of compression or expansion has reached a predetermined measure. As a result of the engagement of the first hook and the second hook preventing any further movement of the spring bracket in terms of the neck region, any further deformation of the spring bracket, and consequently damage to the torque wrench, can be prevented.

In one preferred embodiment of the torque wrench, the spring bracket is configured on that side of the neck region that faces away from the activation lever, and configured so as to project from said neck region. This arrangement enables simple handling of the torque wrench when the latter is used in the mouth of the patient.

The spring bracket is preferably configured so as to be integral to and in one piece with the neck region. This simplifies the cleaning, because the absence of a connecting location between the neck region and the spring bracket prevents any deposition of dirt at the connecting location.

In one preferred embodiment of the torque wrench, a portion of the spring bracket has a reduced cross section so as to dimension the force which, by the spring bracket, is exerted at least approximately in the radial direction on the inserted driver instrument. This construction can be readily implemented in the production of the torque wrench and forms a favorable variant for achieving the desired force of the spring bracket. The reduction of the cross section of the spring bracket aims at reducing the force of the spring bracket such that the torque transmitted by friction to the driver instrument is minimal in the releasing position of the latching cam. As a result, any undesirable unscrewing of the implant or of the connecting element in the releasing position can be avoided.

The portion of the spring bracket having the reduced cross section can be formed by a recess in the spring bracket. For example, this recess can be formed by an incision in the spring bracket that runs so as to be radial to the rotation axis. Using the same material for the spring bracket, it is however also possible for a constant but thinner cross section of the spring bracket across the entire length of the spring bracket to be selected in order for the same exerted force to be achieved. The determination of the force of the spring bracket in this case is simple, but the thin cross section may form a weak point in specific materials. Furthermore, it is also possible for the exerted force of the spring bracket to be dimensioned by selecting a matching material. Depending on the conditions which have to be met when dimensioning the force of the spring bracket, the person skilled in the art may select one of the solutions mentioned above or combine these solutions.

In one preferred embodiment of the torque wrench, the bezel is configured so as to be at least approximately annular. This shape of the bezel matches a majority of the driver instruments so that the torque wrench can be widely used. Furthermore, this shape can be produced in a simple and cost-effective manner.

In one particularly preferred embodiment of the torque wrench having an at least approximately annular bezel, a tangent to that circumferential face of the spring bracket that faces the rotation axis, at a point of the portion where the spring bracket, when measured in the radial direction, has the at least approximately smallest cross section, extends so as to be at least approximately parallel to a radius, which radius runs from the rotation axis to the entrainment portion. However, it is also possible for the tangent to be designed so as to be at least approximately parallel to a normal in terms of the engagement face, the latter preferably being a plane. These arrangements offer an optimal distribution of the stresses in the bezel so that the risk of breakage or of a non-elastic deformation of the spring bracket can be reduced.

When dimensioning the force which is exerted by the spring bracket onto the driver instrument during the rotation counter to the tightening direction, it has to be ensured that the transmitted torque, that is to say the torque that is transmitted in the releasing position of the latching cam, does not exceed a predetermined torque limit value which could lead to the implant, or the connecting element, respectively, being unscrewed. The torque wrench can thus fulfill the ratchet function thereof when rotating counter to the tightening direction.

In one preferred embodiment, the torque wrench has an indicator region which, from the neck region, projects on that side of the neck region that faces away from the head region, projects in a shaft region that extends so as to be at least approximately parallel to the plane, and projects from the free end region of the shaft region, wherein the activation lever extends at least up to the indicator region. The activation lever preferably extends into the indicator region.

The activation lever is preferably configured so as to be in one piece with and integral to the neck region so as to simplify the cleaning.

The activation lever particularly preferably extends beyond the indicator region so as to enable a simple operation of the activation lever by way of the portion of the latter that extends beyond the indicator region.

A resting position, or a deflecting position, respectively, of the activation lever defines the position of the latter when no force, or a force, respectively, is exerted on the activation lever, that is to say when the activation lever is not bent, or is bent, respectively.

The shaft region, when viewed in the tightening direction, is preferably fastened to the neck region downstream of the activation lever, and the shaft region preferably runs parallel to the activation lever which is situated in the resting position of the latter. This arrangement offers a compact shape of the torque wrench such that the torque wrench occupies little space in the surgical cassette. Furthermore, the torque wrench and other tools thus do not engage with one another in the surgical cassette.

A gap between the shaft region and the activation lever is preferably present so as to enable easy cleaning.

The indicator region, for example in the shape of a small plate, preferably likewise extends so as to be at least approximately parallel to the plane. The indicator region is particularly preferably configured so as to be in one piece with and integral to the shaft region. This embodiment is particularly simple in terms of construction, and the production of said embodiment is cost-effective.

It is likewise possible for the shaft region to be configured with a first arm and a second arm which extend so as to be at least approximately parallel to the plane and extend from the neck region on that side that faces away from the head region, wherein the free end of the first arm and of the second arm are connected by way of the indicator region, and the activation lever is disposed on the neck region between the first arm and the second arm. The first arm and the second arm conjointly with the indicator region form a handle, preferably in the form of an acute triangle, permitting simple handling of the torque wrench, in particular when the latter is being placed onto the driver instrument.

The shaft region is preferably resistant to flexing such that the relative movement of the activation lever in terms of the shaft region can be reproduced in a reliable and simple manner.

In one particularly preferred embodiment of the torque wrench, the activation lever is flexural, preferably elastically flexural, particularly preferably flexural in a linear-elastic manner. By way of an elastically flexural activation lever it is ensured that flexing remains reversible and the activation lever returns to the original shape thereof when a force is no longer applied. The indication accuracy of the applied torque can thus be guaranteed over the entire service life of the torque wrench. An activation lever which is flexural in a linear-elastic manner has a resultant flexing which is proportional to the force acting thereon, this enabling a reliable and practical operation of the torque wrench.

When a force in the tightening direction is applied to a free end region of the activation lever, a deflection of the activation lever, proceeding from the resting position of the latter, is a measure for the torque generated. The activation lever on the portion thereof that overlaps the indicator region preferably has a dog, and the indicator region preferably has an elongate bore which is specified for receiving the dog. When flexing the activation lever from the resting position thereof at least up a maximum predetermined flexing, the dog moves along the elongate bore. The elongate bore is particularly preferably configured in such a manner that the latter forms a terminal detent for the dog once the flexing of the activation lever corresponds to the maximum torque to be applied. As a result, an excessive expansion and thus a deformation beyond the elastic range of the activation lever can be almost completely avoided.

In an even more preferred embodiment of the torque wrench, measurement marks on which the deflection of the activation lever can be read as the torque generated are attached to the indicator region. The measurement marks are preferably attached along the elongate bore such that the applied torque can be read by way of the position of the dog in the elongate bore in terms of the measurement marks. The dog is preferably configured so as to be flush with the surface of the indicator region such that a parallax error can be avoided when evaluating the congruence of the dog with a measurement mark.

Materials which have already been used medical technology and are biocompatible, able to be cleaned and sterilized, are suitable for producing the torque wrench. Suitable materials here are, for example, metal and metal alloys such as steel, stainless steel, titanium, titanium alloys, and plastics material.

The torque wrench can also be used for releasing the implant or the connecting element, respectively, in that the torque wrench is rotated by 180° about the activation lever and is placed onto the driver instrument again.

Further advantages and characteristics of the invention are derived from the description hereunder of an exemplary embodiment which will be explained by means of the appended figures in which, in a purely schematic manner.

Figure 1:
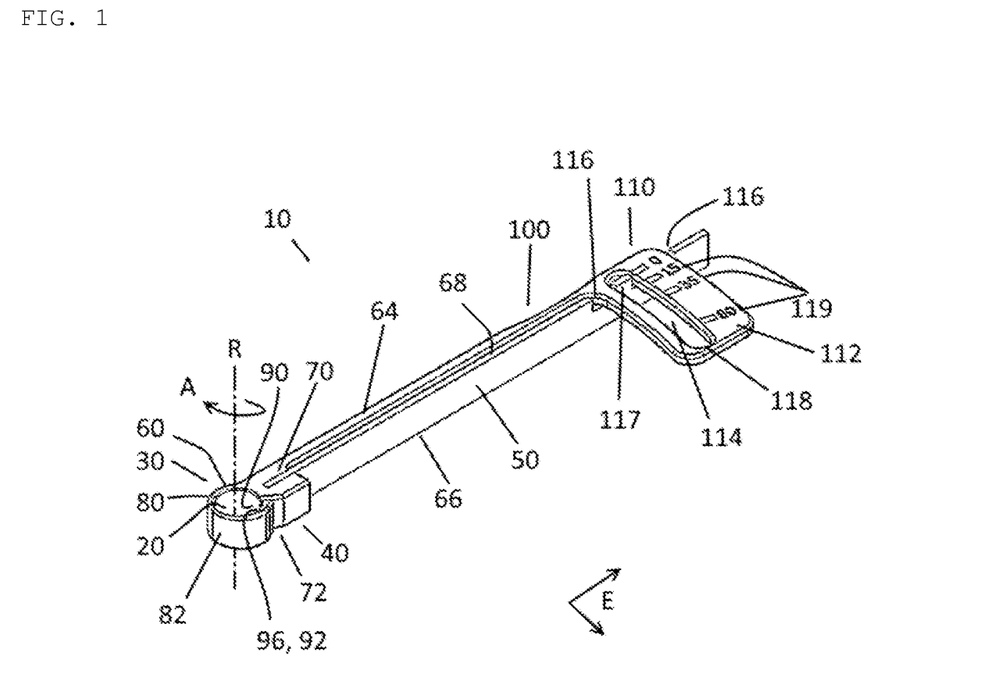
FIG. 1 shows a perspective view of the torque wrench according to the invention.
Figure 2:
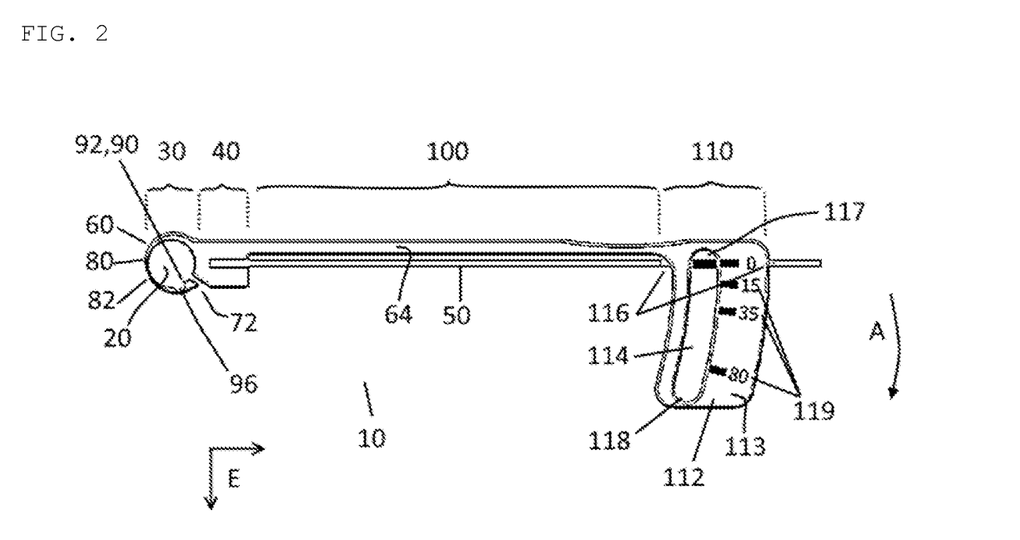
FIG. 2 shows a plan view of the torque wrench according to FIG. 1.
Figure 3:
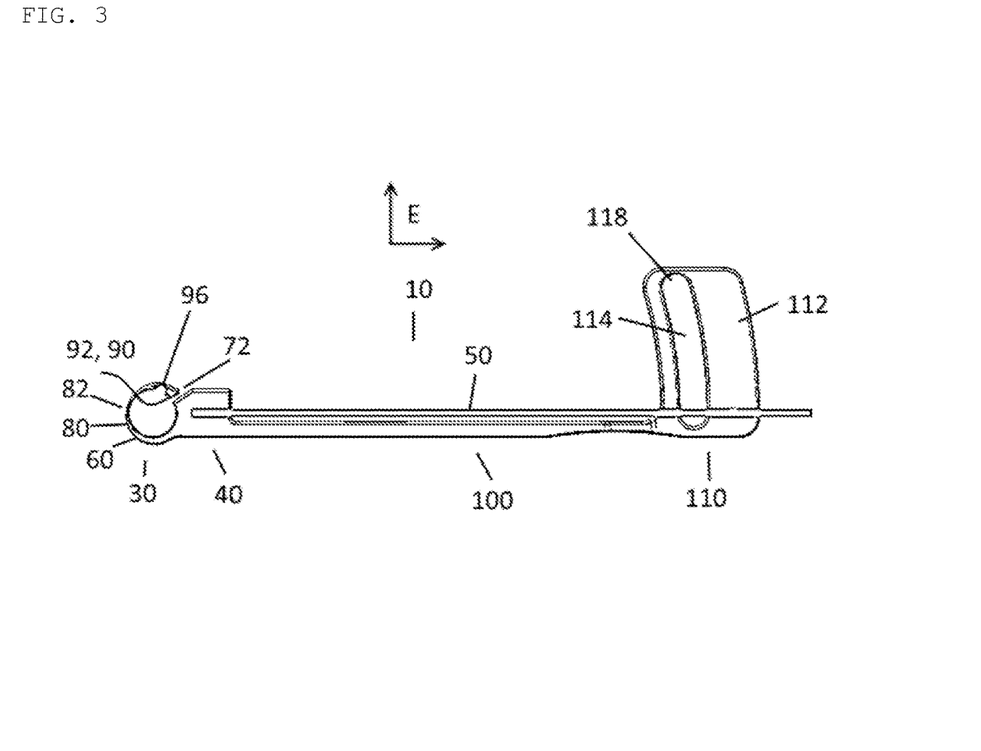
FIG. 3 shows a view of the rear side of the torque wrench according to FIG. 1.

The torque wrench 10 depicted in the sequence of FIGS. 1, 2 and 3 comprises a head region 30 which has a receptacle opening 20 a neck region 40 which adjoins the head region 30, and a bar-shaped, flexural activation lever 50 which is rectangular in the cross section, and, for applying a torque to the head region 30, is fastened to the neck region 40. The receptacle opening 20 of the head region 30 is formed by an annular bezel 60 which defines a rotation axis R. The bezel 60 is specified for receiving a driver instrument 62 in the extent of the rotation axis R, said driver instrument 62 being described in more detail in FIG. 4. A plane E extends so as to be orthogonal to the rotation axis R and comprises a front side 64 of the torque wrench 10, said front side 64 being illustrated in FIG. 2. A rear side 66 of the torque wrench 10 is depicted in FIG. 3.

A front side 68 of the activation lever 50 extends in the plane E. Furthermore, the extent of the cross section of the activation lever 50 in the direction orthogonal to the plane E is larger than in the direction parallel to the plane E.

The neck region 40 forms an at least approximately cuboid, solid part and comprises an incision 70 which, for receiving an end region of the activation lever 50 and fastening the latter, runs so as to be orthogonal to the plane E.

The bezel 60, running across the entire cross section thereof, furthermore has a cutout 72, the bezel 60 forming a spring bracket 80. The spring bracket 80 on that side of the neck region 40 that faces away from the activation lever 50 is configured so as to project from said neck region 40 and so as to be integral to and in one piece with the neck region 40. The cutout 72 is adjacent to the neck region 40 and is formed by a slot 72 which extends so as to be at least approximately radial to the rotation axis R.

A portion 82 of the spring bracket 80 has a reduced cross section which will be described in more detail in FIG. 5.

A latching cam 90 is configured on the spring bracket 80 so as to be adjacent to the cutout and integral to and in one piece with the spring bracket 80. The latching cam 90 in the resting position thereof protrudes into the receptacle opening 20. The resting position is the position of the latching cam 90 when no driver instrument is inserted in the receptacle opening 20 and no force in the radial direction is exerted on the spring bracket 80.

Figure 4:
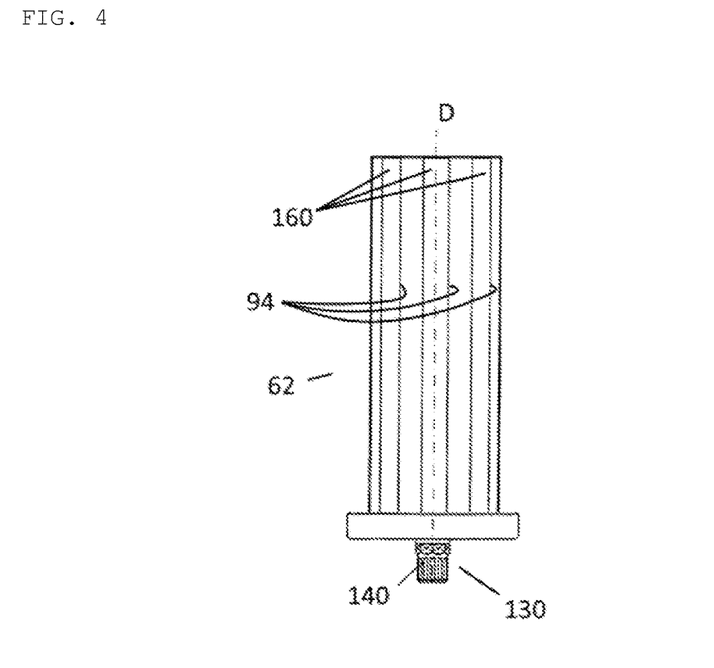
FIG. 4 shows a lateral view of a conventional driver instrument.
Figure 5:
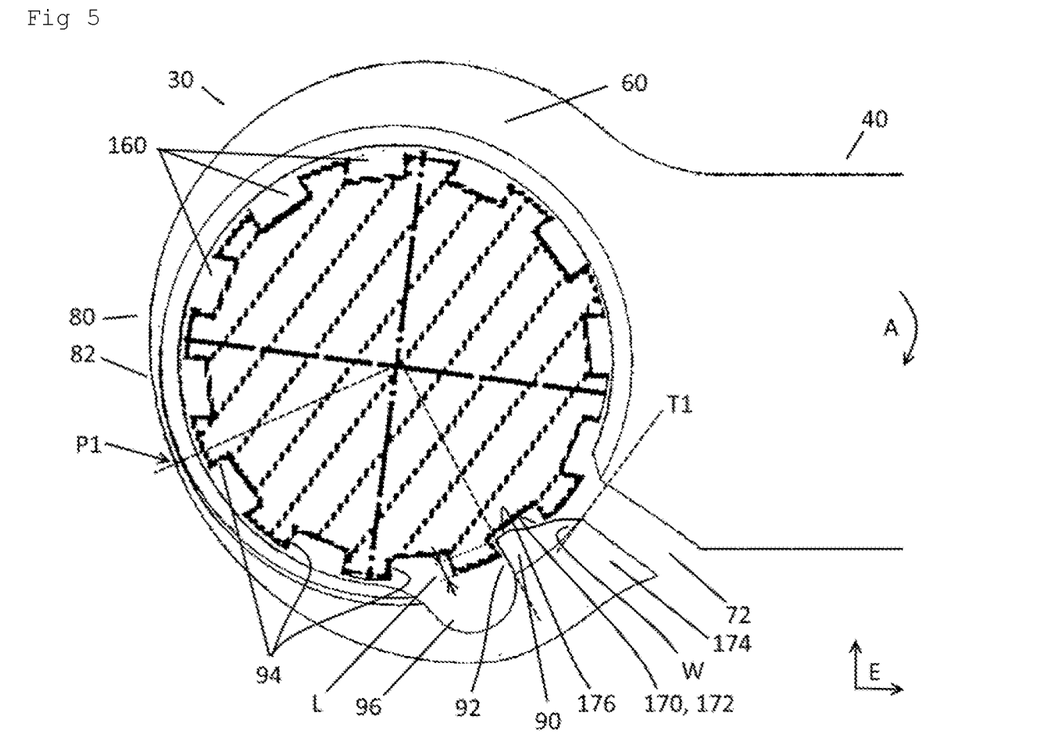
FIG. 5 shows a plan view of the head region having the inserted driver instrument, illustrated in the cross section, of FIG. 4.

The latching cam 90 furthermore has an entrainment portion 92 which, when the driver instrument 62 is inserted in the receptacle opening 20, and when the activation lever 50 is rotated in the tightening direction A in an entraining position of the latching cam 90, is specified for interacting with a mating face 94 of the driver instrument 62, said driver instrument 62 being able to be seen in FIGS. 4 and 5. When the entrainment portion 92 interacts with the mating face 62, a torque is transmitted to the driver instrument 62 by a form-fitting entrainment.

The latching cam 90, when rotating counter to the tightening direction A, is specified for moving counter to the force of the spring bracket 80 in a radially outward direction to a releasing position, so as to form a freewheeling mechanism between the head region 30 and the driver instrument 62.

Moreover, the spring bracket 80 on that side thereof that faces the rotation axis R, when viewed in the tightening direction A, has a semicircular clearance 96 which in terms of the entrainment face 92 is a leading clearance 96 which adjoins the entrainment face 92.

The torque wrench 10 likewise comprises a flexurally resistant shaft portion 100 which on the side of the neck region 40 that faces away from the head region 30, from the head region 40 projects so as to be at least approximately parallel to the plane E, and an indicator region 110 which projects from the free end region of the shaft region 100, wherein the activation lever 50 extends beyond the indicator region 110.

The shaft region 100, when viewed in the tightening direction A, is fastened to the neck region 40 downstream of the activation lever 50, is configured so as to be in one piece with and integral to the neck region 40, and runs parallel to the activation lever 50 which is situated in the resting position thereof, wherein a gap is present between the shaft region 100 and the activation lever 50.

The indicator region 110 extends in the form of a small plate 112 which has a front face 113 which runs in the plane E, and is configured so as to be in one piece with and integral to the shaft region 100.

The activation lever 50 on the portion thereof that overlaps the indicator region 110 has a recess 116 which forms a void 116 for the indicator region 110. The void 116 is configured in such a manner that said void 116, when activating the activation lever 50, permits the movement of the front side 68 of the activation lever 50 in the plane E, that is to say in the same plane as the front face 113 of the small plate 112. The recess 116 is formed by two rectangular incisions, the height of the latter, when measured in the direction orthogonal to the plane E, corresponds at least approximately to the thickness of the small plate 112, said two rectangular incisions being separated by a portion of the activation lever 50 that runs in the plane E. The portion of the activation lever 50 forms a dog 117 which serves as a pointer 117 and, when activating the activation lever 50, moves in an elongate bore 114 configured in the small plate 112. The dog 117 is thus configured so as to be flush with the front face 113 of the indicator region 110. The elongate bore 114 extends in the form of an arc, the center of the latter being defined by way of the center of the curvature of the activated activation lever 50.

When flexing the activation lever from the resting position thereof at least up to a maximum predetermined flexing, the pointer 117 moves along the elongate bore 114. The elongate bore 114 is configured in such a manner that the latter forms a terminal detent 118 for the dog 117 when the flexing of the activation lever 50 corresponds to the maximum torque to be applied.

Measurement marks 119 on which the deflection of the activation lever 50 can be read as a torque generated are attached on the indicator region 110 along the elongate bore 114. When applying a force in the tightening direction A to a free end region of the activation lever 50, a deflection of the activation lever 50, proceeding from the resting position thereof, is a measure for the torque generated.

Torques in the range from 10 Ncm to 100 Ncm are typically required, depending on the tooth implant system.

FIG. 4 shows a conventional driver instrument 62 comprising a cylindrical ratchet head 120 which defines a rotation axis D of the driver instrument and can be inserted in the receptacle opening 20 of the torque wrench 10, and a shaft 130 which adjoins the ratchet head 120 and extends in the direction of the rotation axis D. The free end 140 of the shaft has a standardized profile for interacting with an implant, or a connecting element, respectively, such that the driver instrument 62 can transmit the torque applied to the ratchet head 120 to the implant or to the connecting element, respectively. The ratchet head 120 has a circumferential face 150 which comprises a contour feature which forms the mating face 94, so as to enable a transmission of the torque applied to the torque wrench 10 to the driver instrument 62. The contour feature comprises a plurality of grooves 160 which run so as to be parallel to the rotation axis D of the driver instrument 62 and which are of identical configuration and which, when viewed in the circumferential direction, are disposed at identical mutual spacings. The grooves 160 have an at least approximately rectangular cross section, the wall 94 of said grooves 160 that, in the tightening direction, is the leading wall 94 in terms of the entrainment face preferably running so as to be at least approximately radial in the direction toward the rotation axis D and forming the mating face 94.

The interaction of the entrainment portion 92 of the latching cam 90 with the mating face 94 of the inserted driver instrument 62 in the tightening direction A is illustrated in FIG. 5. The entrainment portion 92 is formed by the entrainment face 92 which runs so as to be at least approximately radial to the rotation axis R and is specified for interacting with the mating face 94 of the inserted driver instrument 62 that runs so as to be at least approximately radial to the rotation axis R.

The length of the entrainment face 92 which is measured radially to the rotation axis R, said entrainment face coming into contact with the mating face 94 of the driver instrument 62, forms the operating length L. The operating length L corresponds to the minimum length of the required movement of the latching cam 90 in a radially outward manner in terms of the rotation axis R, such that the latching cam 90 can reach the releasing position thereof.

The latching cam 90 furthermore has an engagement face 170 which, when viewed in the tightening direction A, trails the entrainment face 92 and adjoins the entrainment face 92, and which permits the movement of the latching cam 90 to the releasing position.

The engagement face 170 is formed by a taper 172, the spacing of the latter from the rotation axis R counter to the tightening direction A increasing without any interruption and permitting the freewheeling mechanism. The taper 172 extends at least approximately up to the free end 174 of the spring bracket 80.

The engagement face 170 moreover comprises an extension face 176 which runs in the circumferential direction and which the entrainment face 92 directly adjoins, and which the taper 172 directly adjoins.

The latching cam 90 is configured such that, when measured in the circumferential direction of the bezel 60, the overall length of the taper 172, conjointly with the extension face 176, is longer than the width of the grooves 160.

An angle W which in the plane E is measured between the taper 172 and a tangent T1 to the circumferential direction that, when viewed in the tightening direction, runs on the trailing final point of the taper in the embodiment illustrated is approximately 30°.

The spring bracket 80 at a point P1, when measured in the radial direction, has the at least approximately smallest cross section. The point P1 is situated opposite the engagement face 170 so as to be offset by at least approximately 90° in the tightening direction. In the embodiment illustrated, the portion 82 of the spring bracket 80 having the reduced cross section extends on both sides of the point P1.

Figure 6:
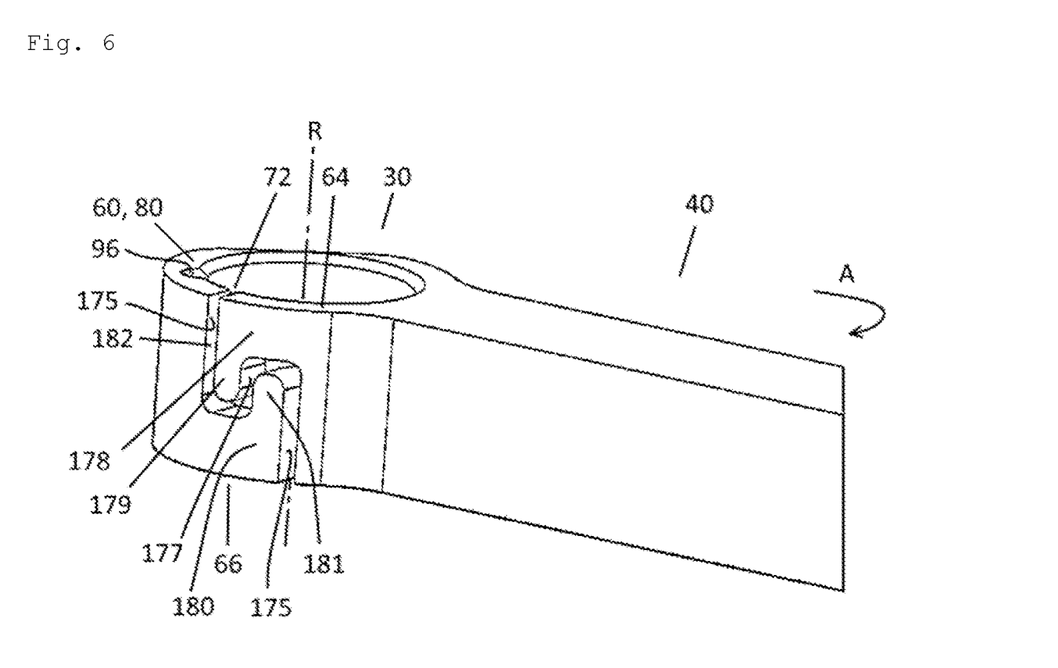
FIG. 6 shows a perspective view of the head region and neck region of a further embodiment of the torque wrench.

A further embodiment of the cutout 72 which is configured by a radially running cutting is illustrated in FIG. 6. The bezel 60 has a thin wall, that is to say a longitudinal section, which in the axial direction is substantially larger than in the radial direction.

The cutout 72 is configured in such a manner that said cutout 72 delimits the movement of the spring bracket 80, in relation to the neck region 40 in the circumferential direction, in the tightening direction A and counter to the tightening direction A.

The spring bracket 80 on the free end 174 thereof has an end face 175 which is defined by the cutout 72 and runs so as to be at least approximately radial to the rotation axis R, and which is faced by a counter-end face 177 of the neck region 40 that is defined by the cutout 72 and runs so as to be at least approximately radial to the rotation axis.

The cutout 72 and thus the end face 175 and the counter-end face 177, when viewed in the longitudinal section of the bezel 60, run so as to be at least approximately S-shaped and from the front side 64 to the rear side 66 of the torque wrench 10, wherein a first half of the S-shape that faces the front side 64 forms a first hook 178 which projects from the neck region 40, and a second half of the S-shape that faces the rear side 66 forms the second hook 180 which projects from the spring bracket 80.

A gap 182 between the first hook 178 and the second hook 180 is present in the resting state and in the normal operation of the torque wrench. The first hook 178 and the second hook 180 have a first protrusion 179 and a second protrusion 181, respectively, which come to bear on one another once the deformation of the spring bracket 80 has reached a predetermined measure, thus preventing any further deformation of the spring bracket 80. It is to be noted here that the deformation can be prevented in the tightening direction as well as counter to the tightening direction.

Figure 7:
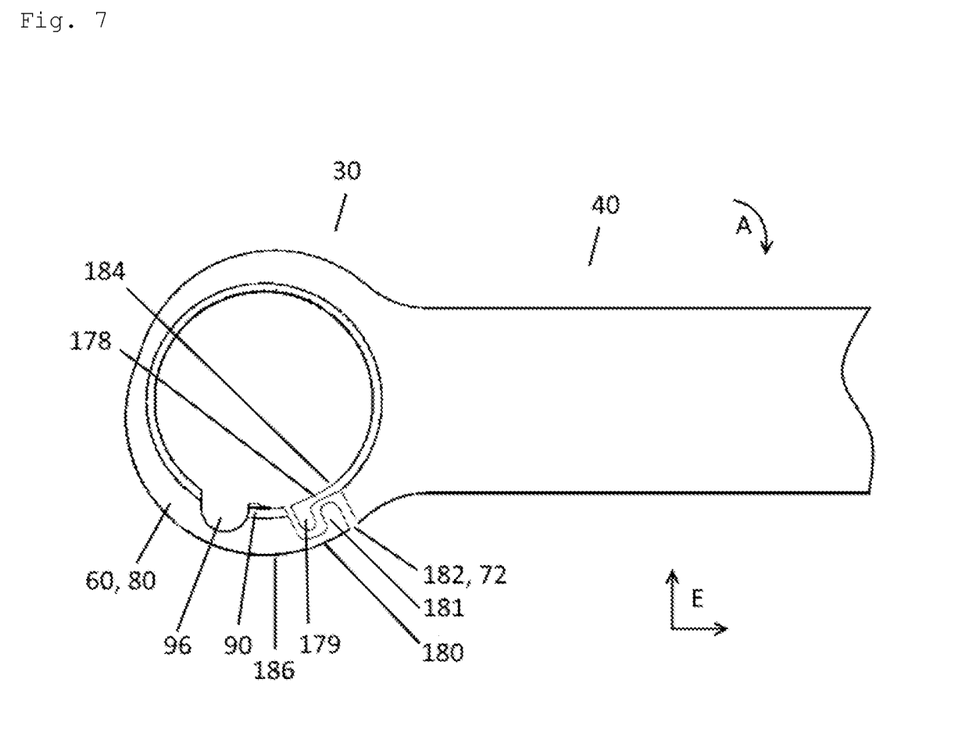
FIG. 7 shows a plan view of the head region and neck region of a further embodiment of the torque wrench.

A further embodiment of the cutout 72 which is configured by an axially running cutting is illustrated in FIG. 7. As opposed to the embodiment of FIG. 6, the bezel 60 has a thick wall.

When viewed in the cross section of the bezel 60, that is to say in a plane that runs parallel to the plane E, the cutout 72 runs so as to be at least approximately S-shaped and from an internal side 184 of the bezel 60 that faces the rotation axis to an external side 186 of the bezel 60 that faces away from the rotation axis. The first half of the S-shape that faces the internal side 184 forms the first hook 178 which projects from the neck region 40, and the second half of the S-shape that faces the external side 186 forms the second hook 180 which projects from the spring bracket 80.

In the event of a deformation of the spring bracket 80, the interaction of the first hook 178 and the second hook 180 and the first protrusion 179 thereof and the second protrusion 181 thereof, respectively, is identical to that of the embodiment of FIG. 6.

Figure 8:
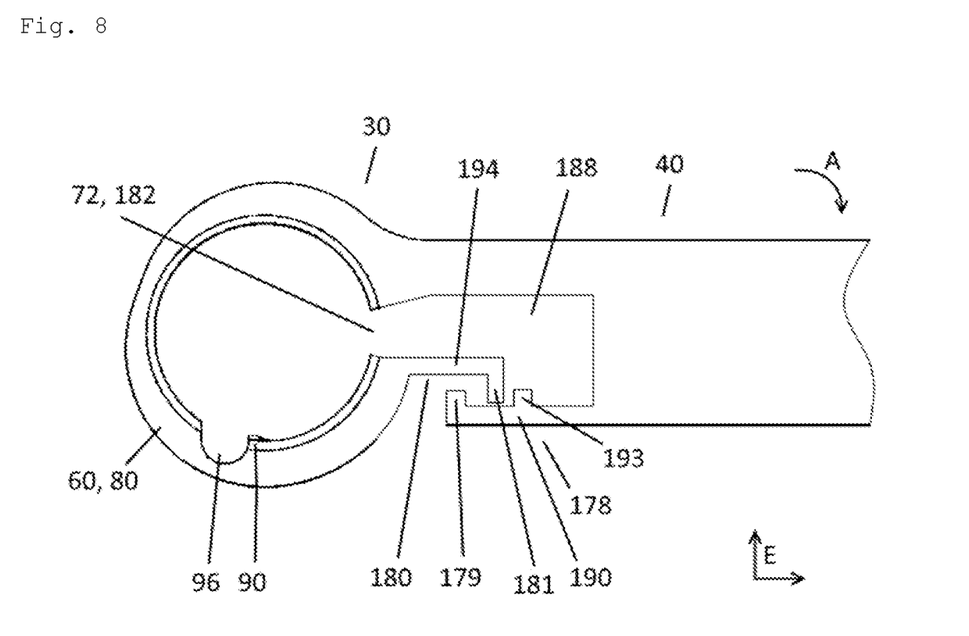
FIG. 8 shows a plan view of the head region and neck region of a further embodiment of the torque wrench.

A further embodiment of the cutout 72 in which the cutout opens out into a rectangular recess 188 which is configured in the neck region 40 and connected to the receptacle opening 20 is illustrated in FIG. 8. The recess 188 has a wall 190 which is directed so as to be at least approximately radial to the rotation axis R and, when viewed in the tightening direction A, is a wall 190 trailing the cutout 72, the second protrusion 179 and a further protrusion 193 projecting from said wall 190 in the direction toward the interior of the recess 188.

The second hook 180 comprises an arm 194 which in terms of the rotation axis R projects radially outward from the spring bracket 80 and which protrudes into the recess 188 and lies between the second protrusion 179 and the further protrusion 193. The free end of the arm 194 has the first protrusion 181 which is directed in the direction toward the wall 190. The first protrusion 181 comes to bear on the second protrusion 179 so as to delimit the movement of the spring bracket 80 by expansion once the deformation of the spring bracket 80 has reached a predetermined measure.

Excessive expansion of the spring bracket 80 can thus be prevented. In contrast, the first protrusion 181 comes to bear on the further protrusion 193 so as to delimit the movement of the spring bracket 80 by compression.

For the sake of completeness, it is to be mentioned that in an embodiment similar to the embodiment of FIG. 8, the first hook 178 may have one protrusion and the second hook 180 may have two protrusions. In an analogous manner, the interaction of the first hook 178 and the second hook 180, and of the respective protrusions thereof in the event of a deformation of the spring bracket 80, is identical to that in the embodiment of FIG. 8.

LIST OF REFERENCE SIGNS

Plane E
Rotation axis R
Operating length L
Tightening direction A
Rotating direction D
Tangent T1
Point P1
Angle W
Torque wrench 10
Receptacle opening 20
Head region 30
Neck region 40
Activation lever 50
Bezel 60
Driver instrument 62
Front side 64
Rear side 66
Front side 68 (of the activation lever)
Incision 70
Cutout, slot 72
Spring bracket 80
Portion of the spring bracket 82
Latching cam 90
Entrainment portion, entrainment face of the latching cam 92
Mating face of the driver instrument 94
Clearance 96
Shaft region 100
Indicator region 110
Small plate 112
Front face 113
Elongate bore 114
Recess, void 116
Dog, pointer 117
Terminal detent 118
Measurement marks 119
Ratchet head 120
Shaft 130
Free end of the shaft 140
Circumferential face 150
Grooves 160
Engagement face 170
Taper 172
Free end of the spring bracket 174
End face 175
Extension face 176
Counter-end face 177
First hook 178
First protrusion 179
Second hook 180
Second protrusion 181
Gap 182
Internal side of the bezel 184
External side of the bezel 186
Recess 188
Wall 190
Arm 194
Further protrusion 193

The invention claimed is:

1. A torque wrench as a ratchet instrument for medical technology, the torque wrench comprising:
a head region including a receptacle opening,
a neck region which adjoins the head region,
a bar-shaped activation lever for applying a torque to the head region, the bar-shaped activation lever being fastened to the neck region and extending at least approximately in one plane,
a bezel which forms the receptacle opening of the head region and defines a rotation axis that runs so as to be at least approximately orthogonal to the plane, the bezel being configured to receive a driver instrument in a direction extending along the rotation axis, and
a spring bracket and a latching cam which is arranged on the spring bracket, wherein:
in a resting position of said latching cam, the latching cam protrudes into the receptacle opening,
the latching cam includes an entrainment portion that is configured to interact with a mating face of the driver instrument so as to transmit a torque to the driver instrument by way of entrainment when the driver instrument is inserted in the receptacle opening, and when the activation lever is rotated in a tightening direction in an entraining position of the latching cam,
the latching cam, when rotating counter to the tightening direction, is configured to move counter to a force of the spring bracket to a releasing position, so as to form a freewheeling mechanism between the head region and the driver instrument,
the bezel includes a cutout running across an entire cross section of the bezel and forms the spring bracket, and
the spring bracket includes a recess on a side of the spring bracket that faces the rotation axis, and, when viewed in the tightening direction, the recess leads an entrainment face of the entrainment portion and adjoins the entrainment face.

2. The torque wrench as claimed in claim 1, wherein the latching cam is integral to and in one piece with the spring bracket.

3. The torque wrench as claimed in claim 1, wherein the latching cam is adjacent to the cutout.

4. The torque wrench as claimed in claim 1, wherein the entrainment face runs so as to be at least approximately radial to the rotation axis and is configured to interact with the mating face of the inserted driver instrument.

5. The torque wrench as claimed in claim 1, wherein the latching cam includes a taper which, when viewed in the tightening direction, trails the entrainment face and adjoins the entrainment face, a spacing of the taper from the rotation axis increasing in a direction counter to the tightening direction and permitting the freewheeling mechanism.

6. The torque wrench as claimed in claim 1, wherein the cutout is adjacent to the neck region.

7. The torque wrench as claimed in claim 1, wherein the spring bracket projects from a side of the neck region that faces away from the activation lever.

8. The torque wrench as claimed in claim 1, wherein a portion of the spring bracket has a reduced cross section so as to dimension the force exerted by the spring bracket at least approximately in a radial direction on the inserted driver instrument.

9. The torque wrench as claimed in claim 1, wherein the bezel is configured so as to be at least approximately annular.

10. The torque wrench as claimed in claim 8, wherein:
the bezel is at least approximately annular,
the portion of the spring bracket having the reduced cross section includes a point that, when measured in the radial direction, has an at least approximately smallest cross section, and
a tangent to a circumferential face of the spring bracket that faces the rotation axis at the point extends so as to be at least approximately parallel to a radius that runs from the rotation axis to the entrainment portion.

11. The torque wrench as claimed in claim 1, further comprising:
a shaft region that extends from a side of the neck region that faces away from the head region, and is at least approximately parallel to the plane, and
an indicator region that projects from a free end region of the shaft region,
wherein the activation lever extends at least up to the indicator region.

12. The torque wrench as claimed in claim 11, wherein the activation lever is flexural, and when a force in the tightening direction is applied to a free end region of the activation lever, a deflection of the activation lever, starting from a resting position thereof, is a measure for the torque generated.

13. The torque wrench as claimed in claim 12, wherein the indicator region includes measurement marks on which the deflection of the activation lever can be read as the torque generated.

14. The torque wrench as claimed in claim 1, wherein the ratchet instrument for medical technology is for dentistry.

15. The torque wrench as claimed in claim 4, wherein the bezel is configured to receive the driver instrument such that the mating face of the driver instrument runs so as to be at least approximately radial to the rotation axis.

16. The torque wrench as claimed in claim 6, wherein the cutout is formed by a slot that extends so as to be at least approximately radial to the rotation axis.

17. The torque wrench as claimed in claim 7, wherein the spring bracket is configured so as to be integral to and in one piece with the neck region.

18. The torque wrench as claimed in claim 11, wherein the activation lever extends into the indicator region.

19. The torque wrench as claimed in claim 11, wherein the activation lever extends beyond the indicator region.

20. The torque wrench as claimed in claim 12, wherein the activation lever is flexural in a linear-elastic manner.

* * * * *